United States Patent [19]

Pauli et al.

[11] Patent Number: 5,252,191
[45] Date of Patent: Oct. 12, 1993

[54] METHOD FOR THE PHOTOCHEMICAL ISOMERIZATION OF ORGANIC COMPOUNDS UNDER THE INFLUENCE OF A PHOTOSENSITIZER

[75] Inventors: Louis F. Pauli; Alphons Dufourny; Robert B. Koolstra, all of Weesp; Hans Wynberg; Wolter Ten Hoeve, both of Groningen, all of Netherlands

[73] Assignee: Duphar International Research B.V., Weesp, Netherlands

[21] Appl. No.: 690,684

[22] Filed: Apr. 24, 1991

[30] Foreign Application Priority Data

Apr. 27, 1990 [EP] European Pat. Off. ......... 90201071.9

[51] Int. Cl.$^5$ .................... C07C 401/00; C07G 13/00
[52] U.S. Cl. ................................................. 204/157.67
[58] Field of Search ..................................... 204/157.67

[56] References Cited

U.S. PATENT DOCUMENTS

| | | | |
|---|---|---|---|
| 4,551,214 | 11/1985 | Hansen et al. | 204/159 |
| 4,582,641 | 4/1986 | Hansen et al. | 260/239 R |
| 4,659,503 | 4/1987 | Eidenschink et al. | 252/299.61 |
| 4,686,023 | 8/1987 | Stevens | 204/157.67 |
| 4,886,625 | 12/1989 | Albarella et al. | 252/500 |
| 4,937,292 | 6/1990 | Slemon | 525/326.8 |
| 5,035,783 | 7/1991 | Goethals et al. | 204/157.67 |
| 5,089,365 | 2/1992 | Kuroda et al. | 430/59 |

OTHER PUBLICATIONS

Synthetic Metals, vol. 18, 1987, pp. 785-790; S. Yanagida et al, "Application of Conducting Polymers as Catalysts For . . . ".
Recueil Des Travaux Chimiques Des Pays-Bas vol. 89, No. 3, Mar. 1970, pp. 261-264, A. E. C. Snoeren et al.
Photochemistry and Photobiology vol. 46, No. 2, 1987, pp. 193-199, J. C. Scaiano et al, "Singlet Oxygen Generating . . . ".
Photochemistry and Photobiology, vol. 41, No. 1, 1985, pp. 1-7, J. P. Reyftmann et al, "Excited State Properties of α-. . . ".

*Primary Examiner*—John Niebling
*Assistant Examiner*—C. Delacroix-Muirheid
*Attorney, Agent, or Firm*—Stevens, Davis, Miller & Mosher

[57] ABSTRACT

The invention relates to a method for the photochemical isomerization of organic compounds, in particular for the photochemical conversion of tachysterol compounds into previtamin D compounds and of trans-vitamin D compounds into cis-vitamin D compounds, under the influence of radiation, by exposing a solution of the organic compound to be converted in the presence of a non-polymeric photosensitizer to light with approx. 300–1,000 nm wavelength, and by then isolating the resulting product, wherein a substituted thiophene derivative having a substantial absorption in said wavelength region is used as the photosensitizer. The invention also relates to a new photosensitizer to be used for said isomerization reaction.

3 Claims, No Drawings

METHOD FOR THE PHOTOCHEMICAL ISOMERIZATION OF ORGANIC COMPOUNDS UNDER THE INFLUENCE OF A PHOTOSENSITIZER

The invention relates to a method for the photochemical isomerisation of organic compounds, in particular for the photochemical conversion of tachysterol compounds into previtamin D compounds and of trans-vitamin D compounds into cis-vitamin D compounds, under the influence of radiation, by exposing a solution of the organic compound to be converted in the presence of a photosensitizer to light with approx. 300-1,000 nm wavelength, and by then isolating the resulting product.

According to U.S. Pat. No. 4,686,023, tachysterol$_2$ or tachysterol$_3$ can be converted photochemically into previtamin D$_2$ or previtamin D$_3$, respectively, by carrying out the irradiation reaction in the presence of anthracene as a photosensitizer. The resulting previtamin D compound easily isomerises under the influence of heat into the corresponding vitamin D compound. In said patent specification it is stated that upon irradiation of tachysterol$_3$ with light from a suitable radiation source, ratios as high as 13:1 previtamin D$_3$ to tachysterol$_3$ can be obtained. Other photosensitizers can also effect the above photochemical conversion, generally however, less effective than anthracene. For example, Snoeren et al. (Recl. Trav. Chim. Pays-Bas 89, 1970, 261-264) have investigated fluorenone, benzil and anthraquinone as photosensitizers. These and other sensitizers have been described by Denny et al. in Nouv. J. Chim. 2, 1978, 637-641. Furthermore, certain fused aromatic ring compounds are disclosed as photosensitizers for the above conversion in European pat. appln. 130509.

The above known conversions, however, in particular the photochemical conversion of tachysterol compounds into previtamin D compounds, are still unsatisfactory. In connection with the intended use, viz. for human or veterinary administration, the final vitamin D compound obtained should be produced free from detrimental contaminants. This means that the photochemical conversion should preferably yield a single well-defined product with the desired properties. Insufficient conversion and/or the formation of by-products during the conversion reaction produce(s) a contaminated end product. It is often laborious, sometimes even impossible, to purify such reaction 10 products up to a purity suitable for human or veterinary use.

It is the object of the present invention to provide a method for the above photochemical conversion in which the starting organic compound in a single irradiation reaction is converted into the desired product with an improved selectivity.

According to the present invention this object can be achieved by using as the photosensitizer in the method for the photochemical isomerisation, as mentioned in the opening paragraph, a substituted thiophene derivative having a substantial absorption in the wavelength region of approx. 300-1,000 nm. As a matter of fact, it has been found, that the above photochemical conversion can be improved substantially by using such a thiophene derivative according to the invention. For example, it is possible to convert a tachysterol compound in a single irradiation reaction in the presence of a suitable substituted thiophene derivative, absorbing in the said wavelength region, into the corresponding desired previtamin D compound in a pre-vitamin D - tachysterol ratio of 99:1 and a substantially quantitative yield. This will become apparent from the Examples.

More in particular the substituted thiophene derivative to be used as a photosensitizer in the method according to the invention can be characterized by the general formula

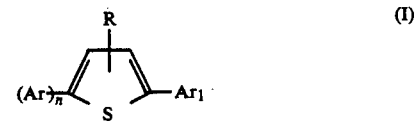

wherein
R is a hydrogen atom or represents one or two substituents selected from the group consisting of C$_1$–C$_4$ alkyl; C$_1$–C$_4$ haloalkyl; C$_3$–C$_6$ cycloalkyl; C$_1$–C$_4$ alkoxy; C$_1$–C$_4$ haloalkoxy; halogen; carboxy; C$_1$–C$_4$ alkoxycarbonyl; nitro; C$_1$–C$_4$ hydroxyalkyl; sulfo; sulfonato; phosphono; phosphonato; unsubstituted or substituted sulfo(C$_1$–C$_4$)alkyl, phosphono(C$_1$–C$_4$)alkyl, sulfonato(C$_1$–C$_4$)alkyl, or phosphonato(C$_1$–C$_4$)alkyl, wherein the substituent is hydroxy or halogen; and amino and amino(C$_1$–C$_4$)alkyl, wherein the amino group may be substituted with one or two C$_1$–C$_4$ alkyl groups, with a C$_2$–C$_5$ alkanoyl group or with a C$_1$–C$_4$ alkoxycarbonyl group, or wherein the amino group may form part of a 5- or 6-membered heterocyclic ring which may comprise a second hetero atom selected from N, O or S;
Ar and Ar$_1$ each independently represents: a phenyl group, a naphthyl group or a heteroaryl group having at least one hetero atom selected from N, O or S, which groups may be substituted with one or more substituents selected from the group consisting of R, as defined above, and a heteroaryl group having at least one hetero atom selected from N, O, S; and
n is 0 or 1;
with the proviso, that if n is 0, Ar$_1$ is an optionally substituted heteroaryl group having at least one hetero atom selected from N, O or S.

Suitable examples of heteroaryl groups having at least one hetero atom selected from N, O or S are pyrrolyl, N-(lower alkyl)pyrrolyl, pyridyl, furyl and thienyl.

It is known that some of the substituted thiophene derivatives covered by the above general formula I are singlet oxygen sensitizers and consequently can be used in photooxidation reactions. Bakker, Gommers, Nieuwenhuis and Wynberg first have shown α-terthiophene to be a photosensitizer for the production of singlet oxygen: J. Biol. Chem. 254, 1979, 1841-1844. Scaiano et al. (Photochem. Photobiol 46, 1987, 193-199) have investigated the singlet oxygen generating efficiency of several substituted thiophene derivatives like terthienyls substituted with methyl, cyano or halogen. Also other thiophene derivatives, for example, having a central phenylene group or pyridylene group have been studied by these researchers, such as dithienylbenzene and dithienylpyridine, as well as naphthyl substituted thiophene Some of the above terthienyls and related compounds like 2,5-diphenylthiophene are disclosed as photosensitizers by Reyftmann et al. in Photochem. Photobiol. 41, 1985, 1-7. Some bithiophenes, such as 5-methyl-2,2'-bithiophene and 5-phenyl-2,2'-bithiophene, have been investigated as singlet oxygen photosensitizers by D'Auria et al. (Gaz. Chim. Ital. 118, 1988, 633–635). In neither of these publications, however, any suggestion is made as to the use of such thiophene derivatives for the above photochemical isomerisation.

It is of advantage to be able to remove the photosensitizer as completely as possible from the resulting final product, after the photochemical conversion has been carried out. To facilitate removal of the photosensitizer, it is suggested in European pat. appln. 252040 to attach the sensitizer molecules to certain polymers. Because the polymeric photosensitizers thus obtained have solubility characteristics which differ from the final product, these polymeric photosensitizers can easily be separated from said product after the photochemical conversion. Sensitizer molecules suitable for attachment to a polymer backbone are anthracenes and substituted anthracenes, provided with a suitable reactive group. Polymeric photosensitizers having a different polymer backbone and their use in photochemical conversions are the subject of the non-prepublished European pat. appln. 89202959.6 in the name of Applicants. These polymeric photosensitizers may comprise photosensitizers derived from substituted thiophene compounds attached to the polymer backbone. The present invention, however, does not include polymeric photosensitizers.

It is an advantage indeed to perform the method of the invention by using a photosensitizer which can easily be removed after completing the photochemical conversion. This advantage can be reached by using as the photosensitizer a substituted thiophene derivative having the general formula

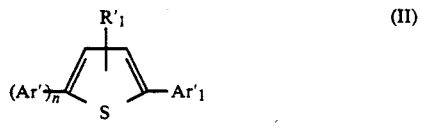

wherein
R' is hydrogen, sulfonato, phosphonato, sulfonato($C_1$-$C_4$)alkyl, hydroxy-substituted sulfonato($C_1$-$C_4$)alkyl, phosphonato($C_1$-$C_4$)alkyl, hydroxy-substituted phosphonato($C_1$-$C_4$)alkyl, amino or amino($C_1$-$C_4$)alkyl, wherein the amino group may be substituted with one or two $C_1$-$C_4$ alkyl groups, or wherein the amino group may form part of a 5- or 6-membered heterocyclic ring which may comprise a second hetero atom selected from N, O or S;
Ar' and Ar'$_1$ each independently represents a phenyl group, a naphthyl group, a thienyl group, a pyridyl group, a pyrrolyl group, a N-(lower alkyl)pyrrolyl group or a furyl group, which groups may be substituted with one or two substituents selected from the group consisting of R', as defined above, and halogen, $C_1$-$C_4$ alkyl, $C_3$-$C_6$ cycloalkyl, $C_1$-$C_4$ alkoxy and thienyl; and
n is 0 or 1;
with the provisos that:
(i) if n is 0, Ar'$_1$ is an optionally substituted heteroaryl group, having at least one hetero atom selected from N, O or S, and
(ii) if neither Ar' nor Ar'$_1$ represents a pyridyl group, at least one substituent selected from the group consisting of R' and the substituents of Ar' and Ar'$_1$ represents a sulfonato group, a phosphonato group, a sulfonato($C_1$-$C_4$)alkyl group, a hydroxy-substituted sulfonato($C_1$-$C_4$)alkyl group, a phosphonato($C_1$-$C_4$)alkyl group, a hydroxy-substituted phosphonato($C_1$-$C_4$)alkyl group, or a group comprising an amino function.

Preferably the above compound of the general formula II comprises a pyridyl group or an amino function, encompassing both a primary and a secondary and a tertiary amino function. In that case the photosensitizer can be protonated with a suitable acid substance and be removed by a simple after-treatment. This method of removing the photosensitizer from the final product is both simple and efficient. As a matter of fact, after the irradiation reaction has been carried out, the photosensitizer can easily be removed from the final product by a simple washing procedure. If desired, the photosensitizer can be easily recovered from the aqueous phase by deprotonation with a suitable base. In case it is preferred to remove the photosensitizer from a water miscible solvent system, polyacids, e.g., polyacrylic acid or polystyrenesulphonic acid may be used for the after-treatment of the product of the photochemical conversion. In such a treatment polymeric electrolytic complexes are formed which precipitate and can easily be removed by filtration. In both cases even the last traces of photosensitizer can easily be removed from the product. Photosensitizers having the general formula II also include compounds comprising a sulfonato or phosphonato group, thus permitting removal of the photosensitizer by a simple washing procedure with water or a substantially aqueous polvent system, if desired made alkaline. Therefore the use of photosensitizers having the general formula II offers an efficient method of purifying the final product from the photosensitizer.

Photosensitizers satisfying the above general formula II are new. Therefore the present invention also relates to a new photosensitizer to be used for the method as defined above, having the general formula II, wherein the symbols have the above-defined meanings.

Because of their properties, including their favourable behaviour in the above described after-treatment, and in connection with their easy preparative accessibility, photosensitizers are preferred which satisfy the general formula

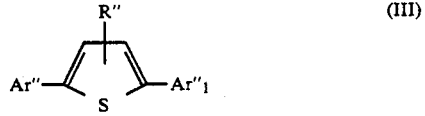

wherein
R" is hydrogen, amino, N,N-dimethylamino, aminomethyl, N,N-dimethylaminomethyl, (1-piperidyl)methyl, (1-piperazinyl)methyl or morpholinomethyl; and Ar" and Ar"$_1$ each independently represent a phenyl group, a thienyl group or a pyridyl group, which groups may be substituted with halogen, methyl or methoxy, or which phenyl group or thienyl group may be substituted with amino, N,N-dimethylamino, aminomethyl, N,N-dimethylaminomethyl, (1-piperidyl)methyl, (1-piperazyl)methyl, (1-pyrimidyl)methyl or morpholinomethyl;
with the proviso, that if neither Ar" nor Ar"$_1$ represents a pyridyl group, at least one substituent selected from the group consisting of R" and the substituents of Ar" and Ar"$_1$ represents a group comprising an amino function.

As indicated above, the last-mentioned photosensitizers can easily be prepared by using methods known as such for related compounds. Thus, in a preferred preparation method, a photosensitizer according to the present invention, having the above general formula III, can be prepared by reacting a diketone of the general formula

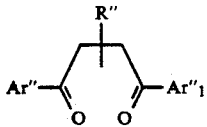

with a suitable sulfurating agent, preferably P₄S₁₀ or Lawesson's reagent, i.e., 2,4-bis(4-methoxyphenyl)-1,3-dithia-2,4-diphosphetane-2,4-disulfide. This reaction is carried out in an inert organic solvent, e.g., an aromatic hydrocarbon like toluene, at a reaction temperature between room temperature and the boiling point of the solvent, preferably at the boiling point of the solvent.

Alternatively, photosensitizers having the general formula

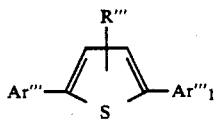

(IV)

wherein
  Ar''' is a phenyl group or a thienyl group, which groups may be substituted with halogen, methyl or methoxy;
  Ar'''₁ is a phenyl group or a thienyl group, which groups may be substituted with aminomethyl or N,N-dimethylaminomethyl; and
  R''' is a hydrogen atom, an aminomethyl group or a N,N-dimethylaminomethyl group;
with the proviso that:
  if Ar'''₁ is an unsubstituted phenyl group or thienyl group, R''' is not a hydrogen atom;
can be prepared by reacting the corresponding compound of formula IV, wherein Ar₁''' comprises a formyl group and/or R''' is a formyl group, with a suitable aminating agent, followed by a reduction and, if desired, by a methylation A suitable aminating agent is, for example, hydroxylamine, ammonia or a primary amine, which in a condensation reaction with the formyl group forms a-CH=N-compound. Said compound can be reduced, e.g., with a suitable reducing agent like SnCl₄, a hydride such as sodiumborohydride or lithiumaluminiumhydride, or hydrogen under the influence of a catalyst. If desired, the amino or aminomethyl substituted compound may be converted to the corresponding N,N-dimethylamino compound by a reaction with a methylating agent like a methylhalogenide or dimethylsulphate. The first-mentioned amination reaction is carried out in an inert solvent like ethanol or aqueous ethanol, preferably at elevated temperature, e.g., at the boiling point of the solvent.

Examples of very suitable new photosensitizers according to the invention are:
(1) 5-aminomethyl-2,2':5',2''-terthiophene,
(2) 3'-N,N-dimethylaminomethyl-2,2':5',2''-terthiophene,
(3) 3'-morpholinomethyl-2,2':5',2''-terthiophene,
(4) 3-N,N-dimethylaminomethyl-2,5-diphenylthiophene,
(5) 3-morpholinomethyl-2,5-diphenylthiophene,
(6) 3-N,N-dimethylaminomethyl-2,5-bis(4-methoxyphenyl)thiophene,
(7) 5-(3-pyridyl)-2,2'-bithiophene,
(8) 5-(2-pyridyl)-2,2'-bithiophene,
(9) 5-(4-pyridyl)-2,2'-bithiophene,
(10) 2-phenyl-5-(2-pyridyl)thiophene,
(11) 2-phenyl-5-(3-pyridyl)thiophene,
(12) 2-phenyl-5-(4-pyridyl)thiophene,
(13) 3'-(3-sulfonatopropyl)-2,2':5',2''-terthiophene, K salt,
(14) 5-sulfonato-2,2':5',2''-terthiophene, Na-salt,
(15) 5,5''-disulfonato-2,2':5',2''-terthiophene, bis-K-salt, and,
(16) 5-(α-hydroxyphosphonatomethyl)-2,2':5',2''-terthiophene, Na-salt.

Other thiophene compounds, known per se, which can be used as photosensitizers in the isomerisation reaction of the invention are:
(17) α-terthiophene
(18) 2,5-di(2-thienyl)furane,
(19) 2,5-di(2-thienyl)pyrrole,
(20) 2,5-di(2-thienyl)-N-methylpyrrole,
(21) 5-phenyl-2,2'-bithiophene,
(22) 2,5-diphenylthiophene,
(23) 5,5'-dichloro-2,2'-bithiophene, and
(24) 5-methyl-2,2'-bithiophene.

The invention will now be described in greater detail with reference to the following specific examples.

EXAMPLE I (a) Preparation of 1,4-di(2-thienyl)-2-morpholinomethyl-1,4-butadione

The starting compound 1,4-di(2-thienyl)-1,4-butadione is prepared according to the method described by Stetter in Angew. Chem. Int. Ed. Engl. 15, 1976, 639. 4,4'-Methylenebismorpholine in a quantity of 9.35 g is dissolved in 40 ml of acetonitrile. Under nitrogen 4.3 g of acetylchloride is added to this solution while stirring and cooling in ice. Then 12.5 g of the above diketone, dissolved in 100 ml of acetonitrile, is added. After stirring at 60° C. for 2 h the reaction mixture is diluted with 100 ml water. The precipitate is filtered off. Thereupon the filtrate is reduced by evaporation and extracted twice with chloroform. The chloroform layers are dried and reduced by evaporation, yielding 20 g of a red oil. After addition of 2N hydrochloric acid, the mixture is washed twice with chloroform. The aqueous layer is made alkaline with a sodiumhydroxide solution and extracted twice with chloroform. After drying and evaporating the solvent, the title compound is obtained as an oily substance in a yield of 3.4 g. A second portion of the title compound is obtained by evaporating the former chloroform layer, adding 150 ml toluene and shaking with a 2N sodiumhydroxyde solution. The aqueous layer is then extracted with toluene. The combined toluene layers are dried and evaporated, yielding another 6.5 g of oily product. ¹H-NMR (CDCl₃): 2.0–2.7 (m.6H); 3.2–3.6 (m.6H); 4.0–4.4 (m. 1H); 6.9–7.8 (m.6H).

(b) Preparation of 3'-morpholinomethyl-2,2':5',2''-terthiophene (3)

The obtained morpholinomethylene diketone in a i.e., 2,4-bis(4-methoxyphenyl)-1,3-dithia-2,4-diphosphetane-2,4-disulfide, are dissolved in 100 ml of toluene; the reaction mixture is refluxed for 4 h while stirring. After cooling down, 100 ml of 2N sodium hydroxide solution is added and the mixture is stirred for 30 min. The layers are separated and the water layer is extracted twice with toluene. The combined toluene layers are extracted with 2N hydrochloric acid. The combined water layers are made alkaline with a sodium hydroxide solution and extracted twice with chloroform. After drying and evaporating the solvent, the title compound (3) is obtained as an oil in a yield of 5.4 g; the oil solidifies upon storage. The solid substance is recrystallized from abs. ethanol, yielding the desired product as a crystalline material with a m.p. of 83°-8° C. 1H-NMR (CDCl$_3$): 2.5(t.4H); 3.5(s.2H); 3.7(t.4H); 6.9-7.5(m.7H). In a corresponding manner as described above the following compounds are prepared:

via 1,4-diphenyl-2-N,N-dimethylaminomethyl-1,4-butadione as the intermediate, the final product: 3-N,N-dimethylaminomethyl-2,5-diphenylthiophene (4); $^1$H-NMR (CDCl$_3$): 2,2 (s.6H); 3.4 (s.2H); 7.0–7.9 (m.10H); HCl-salt, m.p. 195°-196 ° C. (decomp.).

via 1,4-diphenyl-2-morpholinomethyl-1,4-butadione as the intermediate, the final product: 3-morpholinomethyl-2,5-diphenylthiophene (5); m.p. 125°-126° C.;

via 1,4-bis(4-methoxyphenyl)-2-N,N-dimethylaminomethyl-1,4-butadione as the intermediate, the final product: 3-N,N-dimethylaminomethyl-2,5-bis(4-methoxyphenyl)thiophene (6); m.p. 74°-75° C.; and via 1,4-di(2-thienyl)-2-N,N-dimethylaminomethyl-1,4-butadione as the intermediate, the final product: 3'-N,N-dimethylaminomethyl-2,2':5',2''-terthiophene (2); HCl-salt, m.p. 183°-184 ° C.

EXAMPLE II (a) Preparation of 1-(3-pyridyl)-4-(2-thienyl)-1,4-butadione

Powdered NaCN in a quantity of 1.0 g is suspended in 10 ml of dry dimethylformamide while stirring and cooling on ice. To this suspension 18.3 g of 3-dimethylamino-1-(2-thienyl)-1-propanone, dissolved in 15 ml of dimethylformamide, is added under nitrogen. Then 10.7 g of distilled 3-pyridinecarboxaldehyde in 10 ml of dimethylformamide is added. The resulting reaction mixture is stirred at room temperature for 60 h. Upon pouring onto 120 ml of water a red oil is formed. Decantation followed by stirring of the oil with water gives a solid substance, which, after filtration and washing with EtOH/H$_2$O (1:1), yields 15 g of an orange solid. Stirring with EtOH/H$_2$O (4:1) and addition of water yields, after sucking off and drying, 8.0 g of the title compound as a white solid. The filtrate, before the washing operation with EtOH/H$_2$O (1:1), and the decanted water layer are extracted twice with dichloromethane. The organic layers are washed with water and evaporated after drying; then the resulting reddish-brown oil is stirred with EtOH/H$_2$O. The substance solidifies and is stirred again with EtOH/H$_2$O (1:4) for 30 min. The white solid is sucked off under vacuum, yielding another 5.6 g of the title compound. $^1$H-NMR (CDCl$_3$): 3.4 (s.4H); 6.9-9.3 (m.7H).

(b) The diketone obtained is converted into 5-(3-pyridyl)-2,2'-bithiophene (7) in a corresponding manner as described in Example I (b). The final product has a melting point of 86°-87° C.; 1H-NMR (CDCl$_3$): 6.9-7.3 (m.5Ar-H+1Py-H); 7.8 [dt (8;1.5 Hz).1Py-H]; 8.5 [dd (5;1.5 Hz).1Py-H]; 8.8 [d(2 Hz).1Py-H].

In a corresponding manner as described above the following compounds are prepared:

via 1-(4-pyridyl)-4-(2-thienyl)-1,4-butadione as the intermediate, the final product: 5-(4-pyridyl)-2,2'-bithiophene (9); m.p. 119°-121° C.;

via 1-phenyl-4-(2-pyridyl)-1,4-butadione as the intermediate, the final product: 2-phenyl-5-(2-pyridyl)thiophene (10); m.p. 103°-105° C.;

via 1-phenyl-4-(3-pyridyl)-1,4-butadione as the intermediate, the final product: 2-phenyl-5-(3-pyridyl)thiophene (11); m.p. 108°-110° C.; and via 1-phenyl-4-(4-pyridyl)-1,4-butadione as the intermediate, the final product: 2-phenyl-5-(4-pyridyl)thiophene (12); m.p. 181,5°-182,5° C.

EXAMPLE III

Preparation of 5-aminomethyl-2,2':5',2''-terthiophene (1).

Diisopropylamine in a quantity of 3.1 ml is added to 15 ml of dry tetrahydrofuran under nitrogen. To this mixture, cooled down to −78° C., is added 8.8 ml of 2.5 N n-butyllithium in hexane. After stirring at −78° C. for 30 min a solution of 2.5 gα-terthiophene in 15 ml of dry tetrahydrofurane is added dropwise. After stirring for 1 h, 2.3 ml of dimethylformamide is added dropwise to the stirred mixture. The mixture is then in 3 h slowly warmed up to room temperature and poured onto a mixture of dichloromethane and 2N hydrochloric acid, after which the layers are separated. The water layer is again extracted with dichloromethane. The combined organic layers are dried and subjected to flash chromatography with toluene/methylethylketone (100/0→85/15) as the eluent. The desired 5-formyl-2,2':5',2''a-terthiophene is obtained in a yield of 1.84 g.

The above substituted terthiophene in a quantity of 1.5 g is suspended in 10 ml of 96% ethanol. Hydroxylamine.HCl is added in a quantity of 0.39 g, together with 4 ml of water. The mixture is refluxed for 2½ h, cooled down and filtered. The solid product obtained is washed with diethyl ether and dried, yielding 1.4 g of 5-hydroxyiminomethyl-2,2':5',2''-terthiophene.

A volume of 1.65 ml tin(IV)chloride and 0.76 g of sodium borohydride are added at 0° C. to 30 ml of 1,2-dimethoxyethane. The above-obtained oxime in a quantity of 1.5 g is added portion-wise to the above mixture, after which the reaction mixture is stirred overnight at room temperature. Then a mixture of water and a 2N NaOH solution is added while cooling on ice, after which the product is extracted with ethyl acetate. The ethyl acetate layer is treated with 2N hydrochloric acid and the product is filtered. The desired 5-aminomethyl-2,2':5',2''-terthiophene (1) is obtained, after drying, in a yield of 0.6 g; UV-abs. spectrum: $\lambda_{max}$=355 nm, $\gamma$=20,000.

EXAMPLE IV

Preparation of 5-(N-ethoxycarbonyl)amino-2,2'-bithiophene.

Bithienylcarboxylic acid in a quantity of 12.3 g is refluxed with 25 ml thionylchloride for 30 min. After evaporating in vacuo the residual carbonylchloride is obtained in a yield of 13.7 g; m.p. 74° C. The carbonylchloride is converted to the corresponding azide by adding a solution of 1.6 g sodium azide in 5 ml water to a solution of said carbonylchloride in 25 ml of acetone. After 30 min at 0° C., ice water is added and the solid is sucked off. After drying 5-azido-carbonyl-2,2'-bithiophene is obtained in a yield of 4.6 g; m.p. 76° C. A mixture of the azidocompound (4.6 g) and 50 ml of abs. ethanol is refluxed for approximately 8 h. After decoloration with charcoal, the filtrate is evaporated and the residue is crystallized from petroleum ether. The desired 5-ethoxycarbonylamino-2,2'-bithiophene is obtained in a yield of 2.4 g; m.p. 98° C. Elementary analysis: 52.45% C (calc. 52.15), 4.36% H (calc. 4.38), 5.63% N (calc. 5.53) and 25.73% S (calc. 25.32).

EXAMPLE V

Photochemical isomerisation of tachysterol to previtamin $D_3$.

In a typical irradiation experiment 34 mg of terthiophene is dissolved in approximately 50 ml methyl tert. butyl ether (MTBE). To this mixture is added a solution of approx. 200 mg tachysterol in hexane. Tachysterol is freshly prepared from its 3,5-dinitro-4-methyl benzoate by saponification under nitrogen. Then the total volume is made up to 100 ml by adding MTBE. The irradiation is performed in a nitrogen atmosphere at 4° C. in a merry-go-round apparatus, using a high-pressure mercury lamp as light source. The wavelengths below 300 nm are filtered off by means of a filter solution consisting of a mixture of $NaBr$, $Ag_2SO_4$ and $HgSO_4$ in water. The photochemical reaction is monitored by means of HPLC-analysis. After 9 minutes of irradiation previtamin $D_3$ is obtained in a yield of 0.218% (w/v), 0.004% (w/v) of tachysterol being present. Consequently, in a very short time a previtamin D:tachysterol ratio can be obtained of 98:2.

The above-prepared substituted new thiophene photosensitizers can be used in the above irradiation experiment with approx. the same favourable results. The same holds for the above-described known thiophene derivatives like methyl-, cyano- or halogen-substituted α-terthiophenes, 2,5-diphenylthiophene, and methyl- and phenyl-substituted 2,2'-bithiophenes. In particular, use of 2,5-di(2-thienyl)furane, 2,5-di(2-thienyl)pyrrole and 2,5-di(2-thienyl)-N-methylpyrrole as photosensitizer instead of α-terthiophene effects the above conversion in previtamin D: tachysterol ratios of 99:1, 96:4 and 98:2, respectively.

EXAMPLE VI

Photochemical isomerisation of tachysterol to previtamin $D_3$ and removal of the photosensitizer by acidic washing.

The photochemical isomerisation of tachysterol to previtamin $D_3$ is performed in the way as described in Example V. Instead of α-terthiophene, however, 30 mg of 3'-N,N-dimethylaminomethyl-2,2':5'2''-terthiophene (2) are added to the solution as a photosensitizer.

Twelve minutes of irradiation results in a previtamin $D_3$: tachysterol ratio of 99:1 in a yield of 96%. After irradiation, the solvent is removed by evaporation and heptane is added. The sensitizer is removed from the organic layer by some washings with 0.1N-hydrochloric acid. The partition coefficient of the above photosensitizer over 0.1N HCl/heptane is 60, according to UV-analysis.

EXAMPLE VII

Photochemical isomerisation of trans-vitamin $D_3$ to cis-vitamin $D_3$.

Trans-vitamin $D_3$ (100 mg) and 15 mg 5-(3-pyridyl)-2,2'-bithiophene are dissolved in 50 ml methyl tert.butyl ether. This solution is irradiated as described in Example V. After an irradiation time of 30 minutes the ratio cis-vitamin $D_3$ to trans-vitamin $D_3$ in the irradiation mixture is 97:3 (LC-analysis; detection: 254 nm). The photosensitizer is easily removed from the irradiation mixture in the same manner as described in Example VI, using 1N hydrochloric acid as the acid. The partition coefficient of the photosentisizer, used in this experiment, over 1N HCl/heptane is approx. 15, according to UV-analysis.

We claim:

1. A method for the photochemical conversion of tachysterol compounds into previtamin D compounds and of trans-vitamin D compounds into cis-vitamin D compounds, under the influence of radiation, by exposing a solution of the organic compound to be converted in the presence of a non-polymeric photosensitizer to light with approx. 300–1,000 nm wavelength, and by then isolating the resulting product, said method being characterized in that a substituted thiophene derivative having a substantial absorption in said wavelength region is used as the photosensitizer.

2. A method as claimed in claim 1, characterized in that the substituted thiophene derivative to be used as the photosensitizer, has the general formula

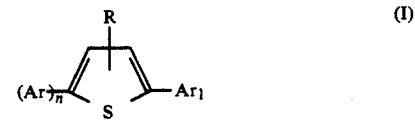

wherein
R is a hydrogen atom or represents one or two substituents selected from the group consisting of $C_1$–$C_4$ alkyl; $C_1$–$C_4$ haloalkyl; $C_3$–$C_6$ cycloalkyl; $C_1$–$C_4$ alkoxy; $C_1$–$C_4$-haloalkoxy; halogen; carboxy; $C_1$–$C_4$ alkoxycarbonyl; nitro; $C_1$–$C_4$ hydroxyalkyl; sulfo; sulfonato; phosphono; phosphonato; unsubstituted or substituted sulfo($C_1$–$C_4$)alkyl, phosphono($C_1$–$C_4$)alkyl, sulfonato($C_1$–$C_4$)alkyl or phosphonato($C_1$–$C_4$)alkyl, wherein the substituent is hydroxy or halogen; and amino and amino ($C_1$–$C_4$)alkyl, wherein the amino group may be substituted with one or two $C_1$–$C_4$ alkyl groups, with a $C_2$–$C_5$ alkanoyl group or with a $C_1$–$C_4$ alkoxycarbonyl group, or wherein the amino group may form part of a 5- or 6-membered heterocyclic ring which may comprise a second hetero atom selected from N, O or S;

Ar and $Ar'_1$ each independently represents:
a phenyl group, a naphthyl group or a heteroaryl group having at least one hetero atom selected from N, O or S, which groups may be substituted with one or more substituents selected from the group consisting of R, as defined above, and a heteroaryl group having at least one hetero atom selected from N, O or S; and n is 0 or 1:

with the proviso, that if n is 0, $Ar_1$ is an optionally substituted heteroaryl group having at least one hetero atom selected from N, O or S.

3. A method as claimed in claim 2, characterized in that the substituted thiophene derivative to be used as the photosensitizer has the general formula

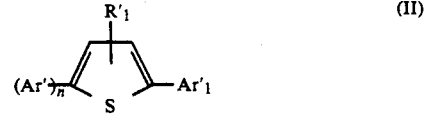

wherein

R' is hydrogen, sulfonato, phosphonato, sulfonato($C_1$-$C_4$)alkyl, hydroxy-substituted sulfonato($C_1$-$C_4$)alkyl, phosphonato($C_1$-$C_4$)alkyl, hydroxy-substituted phosphonato($C_1$-$C_4$)alkyl, amino or amino($C_1$-$C_4$)alkyl, wherein the amino group may be substituted with one or two $C_1$-$C_4$ alkyl groups, or wherein the amino group may form part of a 5- or 6-membered heterocyclic ring which may comprise a second hetero atom selected from N, O or S;

Ar' and $Ar_1'$ each independently represents a phenyl group, a naphthyl group, a thienyl group, a pyridyl group, a pyrrolyl group, a N-(lower alkyl)pyrrolyl group or a furyl group, which groups may be substituted with one or two substituents selected from the group consisting of R', as defined above, and halogen, $C_1$-$C_4$ alkyl, $C_3$-$C_6$ cycloalkyl, $C_1$-$C_4$ alkoxy and thienyl; and n is 0 or 1;

with the proviso that:

(i) if n is 0, $Ar'_1$ is optionally substituted heteroaryl group, having at least one hetero atom selected from N, O or S, and (ii) if neither Ar' nor $Ar'_1$ represents a pyridyl group, at least one substituent selected from the group consisting of R' and the substituents of Ar' and $Ar'_1$ represents a sulfonato group, a phosphonato group, a sulfonato($C_1$-$C_4$)alkyl group, a hydroxy-substituted sulfonato($C_1$-$C_4$)alkyl group, a phosphonato($C_1$-$C_4$)alkyl group, a hydroxy-substituted phosphonato($C_1$-$C_4$)alkyl group, or a group comprising an amino function.

* * * * *